US012685856B2

(12) United States Patent
Malone et al.

(10) Patent No.: US 12,685,856 B2
(45) Date of Patent: Jul. 21, 2026

(54) PERCUTANEOUS CIRCULATORY SUPPORT DEVICE FACILITATING REDUCED HEMOLYSIS

(71) Applicant: Boston Scientific Scimed, Inc., Maple Grove, MN (US)

(72) Inventors: Anthony Malone, Galway (IE); Olena Pernatiy, Galway (IE); Javier Palomar-Moreno, Galway (IE)

(73) Assignee: Boston Scientific Scimed, Inc., Maple Grove, MN (US)

( * ) Notice: Subject to any disclaimer, the term of this patent is extended or adjusted under 35 U.S.C. 154(b) by 851 days.

(21) Appl. No.: 17/974,841

(22) Filed: Oct. 27, 2022

(65) Prior Publication Data

US 2023/0128328 A1     Apr. 27, 2023

Related U.S. Application Data

(60) Provisional application No. 63/272,459, filed on Oct. 27, 2021.

(51) Int. Cl.
*A61M 60/216* (2021.01)
*A61M 60/419* (2021.01)
*A61M 60/869* (2021.01)

(52) U.S. Cl.
CPC ........ *A61M 60/216* (2021.01); *A61M 60/419* (2021.01); *A61M 60/869* (2021.01)

(58) Field of Classification Search
None
See application file for complete search history.

(56) References Cited

U.S. PATENT DOCUMENTS

| | | | |
|---|---|---|---|
| 3,790,180 A | * | 2/1974 | Heyn .................. F16J 15/3244 |
| | | | 277/565 |
| 5,021,048 A | | 6/1991 | Buckholtz |
| 5,049,134 A | * | 9/1991 | Golding ................ F04D 29/047 |
| | | | 417/423.1 |
| 5,145,333 A | | 9/1992 | Smith |
| 5,195,877 A | * | 3/1993 | Kletschka ........... A61M 60/562 |
| | | | 600/16 |

(Continued)

FOREIGN PATENT DOCUMENTS

| | | |
|---|---|---|
| DE | 3338002 A1 | 5/1985 |
| EP | 0847767 B1 | 2/2005 |

(Continued)

OTHER PUBLICATIONS

US 9,067,007 B2, 06/2015, Tanner et al. (withdrawn)

(Continued)

*Primary Examiner* — Carl H Layno
*Assistant Examiner* — Manolis Pahakis
(74) *Attorney, Agent, or Firm* — Seager, Tufte & Wickhem LLP

(57) ABSTRACT

A percutaneous circulatory support device includes an impeller disposed within an impeller housing. The impeller is rotatable relative to the impeller housing to cause blood to flow through the percutaneous circulatory support device. The device further includes a liquid carrier carrying a liquid. The liquid carrier is rotatable relative to the impeller housing to cause the liquid to form outwardly extending menisci at a plurality of apertures of the liquid carrier.

20 Claims, 3 Drawing Sheets

(56)                    References Cited

U.S. PATENT DOCUMENTS

| | | | |
|---|---|---|---|
| 5,211,546 A | 5/1993 | Isaacson et al. | |
| 5,332,361 A * | 7/1994 | Bras | F04D 29/126 |
| | | | 277/916 |
| 5,507,629 A | 4/1996 | Jarvik | |
| 5,527,159 A | 6/1996 | Bozeman, Jr. et al. | |
| 5,575,567 A * | 11/1996 | Brown | F16C 33/1035 |
| | | | 384/100 |
| 5,601,418 A * | 2/1997 | Ohara | A61M 60/546 |
| | | | 417/424.2 |
| 5,611,679 A | 3/1997 | Ghosh et al. | |
| 5,692,882 A | 12/1997 | Bozeman, Jr. et al. | |
| 5,928,131 A | 7/1999 | Prem | |
| 5,947,703 A | 9/1999 | Nojiri et al. | |
| 5,947,892 A | 9/1999 | Benkowski et al. | |
| 5,964,694 A | 10/1999 | Siess et al. | |
| 6,056,520 A | 5/2000 | Nguyen et al. | |
| 6,135,729 A | 10/2000 | Aber | |
| 6,139,487 A | 10/2000 | Siess | |
| 6,176,822 B1 | 1/2001 | Nix et al. | |
| 6,176,848 B1 | 1/2001 | Rau et al. | |
| 6,201,329 B1 | 3/2001 | Chen | |
| 6,227,820 B1 | 5/2001 | Jarvik | |
| 6,264,635 B1 | 7/2001 | Wampler et al. | |
| 6,322,252 B1 * | 11/2001 | Grantz | F16C 33/107 |
| | | | 384/124 |
| 6,446,976 B1 * | 9/2002 | Key | F16J 15/342 |
| | | | 277/369 |
| 6,447,266 B2 | 9/2002 | Antaki et al. | |
| 7,841,976 B2 | 11/2010 | McBride et al. | |
| 7,927,068 B2 | 4/2011 | McBride et al. | |
| 7,972,122 B2 | 7/2011 | Larose et al. | |
| 8,007,254 B2 | 8/2011 | Larose et al. | |
| 8,043,074 B2 | 10/2011 | Tada | |
| 8,376,707 B2 | 2/2013 | McBride et al. | |
| 8,512,012 B2 * | 8/2013 | Akdis | A61M 60/824 |
| | | | 417/423.12 |
| 8,591,393 B2 | 11/2013 | Walters et al. | |
| 8,597,170 B2 | 12/2013 | Walters et al. | |
| 8,684,904 B2 | 4/2014 | Campbell et al. | |
| 8,721,517 B2 | 5/2014 | Zeng et al. | |
| 8,770,945 B2 | 7/2014 | Ozaki et al. | |
| 8,827,661 B2 | 9/2014 | Mori | |
| 8,900,060 B2 * | 12/2014 | Liebing | A61M 60/422 |
| | | | 464/7 |
| 8,992,163 B2 | 3/2015 | McBride et al. | |
| 9,067,005 B2 | 6/2015 | Ozaki et al. | |
| 9,072,825 B2 | 7/2015 | Pfeffer et al. | |
| 9,091,271 B2 | 7/2015 | Bourque | |
| 9,138,518 B2 | 9/2015 | Yuen et al. | |
| 9,162,017 B2 | 10/2015 | Evans et al. | |
| 9,199,020 B2 | 12/2015 | Siess | |
| 9,308,302 B2 | 4/2016 | Zeng | |
| 9,308,304 B2 | 4/2016 | Peters et al. | |
| 9,314,557 B2 | 4/2016 | Ricci et al. | |
| 9,327,067 B2 | 5/2016 | Zeng et al. | |
| 9,364,592 B2 | 6/2016 | McBride et al. | |
| 9,364,593 B2 | 6/2016 | McBride et al. | |
| 9,364,594 B2 | 6/2016 | Nüsser et al. | |
| 9,381,288 B2 | 7/2016 | Schenck et al. | |
| 9,398,743 B1 | 7/2016 | Fox et al. | |
| 9,421,311 B2 | 8/2016 | Tanner et al. | |
| 9,446,179 B2 | 9/2016 | Keenan et al. | |
| 9,616,157 B2 | 4/2017 | Akdis | |
| 9,675,740 B2 | 6/2017 | Zeng et al. | |
| 9,717,833 B2 | 8/2017 | McBride et al. | |
| 9,737,652 B2 | 8/2017 | Larose et al. | |
| 9,770,543 B2 | 9/2017 | Tanner et al. | |
| 9,872,947 B2 | 1/2018 | Keenan et al. | |
| 9,895,476 B2 | 2/2018 | Larose et al. | |
| 9,907,890 B2 | 3/2018 | Muller | |
| 9,956,332 B2 | 5/2018 | Larose et al. | |
| 9,962,475 B2 | 5/2018 | Yuen et al. | |
| 9,964,115 B2 | 5/2018 | Scheckel | |
| 10,029,037 B2 | 7/2018 | Muller et al. | |
| 10,039,872 B2 | 8/2018 | Zeng et al. | |
| 10,071,192 B2 | 9/2018 | Zeng | |
| 10,086,121 B2 | 10/2018 | Fitzgerald et al. | |
| 10,105,475 B2 | 10/2018 | Muller | |
| 10,117,980 B2 | 11/2018 | Keenan et al. | |
| 10,149,932 B2 | 12/2018 | McBride et al. | |
| 10,215,187 B2 | 2/2019 | McBride et al. | |
| 10,232,099 B2 | 3/2019 | Peters et al. | |
| 10,251,985 B2 | 4/2019 | Larose et al. | |
| 10,251,986 B2 | 4/2019 | Larose et al. | |
| 10,478,539 B2 | 11/2019 | Pfeffer et al. | |
| 10,478,540 B2 | 11/2019 | Scheckel et al. | |
| 10,525,178 B2 | 1/2020 | Zeng | |
| 10,537,670 B2 * | 1/2020 | Tuseth | A61M 60/17 |
| 10,576,192 B2 | 3/2020 | Muller et al. | |
| 10,576,193 B2 | 3/2020 | Tanner et al. | |
| 10,704,553 B2 | 7/2020 | Janeczek et al. | |
| 10,709,829 B2 | 7/2020 | Muller | |
| 10,709,830 B2 | 7/2020 | Tanner et al. | |
| 10,765,789 B2 | 9/2020 | Zeng et al. | |
| 10,780,208 B2 | 9/2020 | Siess et al. | |
| 10,786,610 B2 | 9/2020 | Zeng | |
| 10,799,624 B2 | 10/2020 | Pfeffer et al. | |
| 10,842,921 B2 | 11/2020 | Siess et al. | |
| 10,864,308 B2 | 12/2020 | Muller et al. | |
| 10,864,309 B2 | 12/2020 | McBride et al. | |
| 10,874,783 B2 | 12/2020 | Pfeffer et al. | |
| 10,894,115 B2 | 1/2021 | Pfeffer et al. | |
| 10,918,774 B2 | 2/2021 | Stanfield et al. | |
| 10,960,116 B2 | 3/2021 | Yuen et al. | |
| 10,973,967 B2 | 4/2021 | Nyikos et al. | |
| 10,980,927 B2 | 4/2021 | Pfeffer et al. | |
| 11,058,865 B2 | 7/2021 | Fitzgerald et al. | |
| 11,097,092 B2 | 8/2021 | Siess et al. | |
| 11,107,626 B2 | 8/2021 | Siess et al. | |
| 11,123,539 B2 | 9/2021 | Pfeffer et al. | |
| 11,129,978 B2 | 9/2021 | Pfeffer et al. | |
| 11,167,124 B2 | 11/2021 | Pfeffer et al. | |
| 11,219,755 B2 | 1/2022 | Siess et al. | |
| 11,229,786 B2 | 1/2022 | Zeng et al. | |
| 11,235,138 B2 | 2/2022 | Gross-Hardt et al. | |
| 11,253,693 B2 | 2/2022 | Pfeffer et al. | |
| 11,260,213 B2 | 3/2022 | Zeng et al. | |
| 11,273,301 B2 | 3/2022 | Pfeffer et al. | |
| 11,311,712 B2 | 4/2022 | Zeng et al. | |
| 11,338,124 B2 | 5/2022 | Pfeffer et al. | |
| 11,357,967 B2 | 6/2022 | Zeng et al. | |
| 11,400,276 B2 | 8/2022 | Chopra et al. | |
| 11,471,664 B2 | 10/2022 | Xu et al. | |
| 11,497,896 B2 | 11/2022 | Tanner et al. | |
| 11,517,736 B2 | 12/2022 | Earles et al. | |
| 11,565,103 B2 * | 1/2023 | Farago | A61M 60/825 |
| 11,569,015 B2 | 1/2023 | Mourran et al. | |
| 11,583,659 B2 | 2/2023 | Pfeffer et al. | |
| 11,628,294 B2 | 4/2023 | Chopra et al. | |
| 11,648,388 B2 | 5/2023 | Siess et al. | |
| 11,666,748 B2 * | 6/2023 | Kronstedt | A61M 60/13 |
| | | | 600/16 |
| 11,672,968 B2 | 6/2023 | Antaki | |
| 11,708,833 B2 | 7/2023 | McBride et al. | |
| 11,754,075 B2 | 9/2023 | Schuelke et al. | |
| 11,786,700 B2 | 10/2023 | Pfeffer et al. | |
| 11,813,443 B2 | 11/2023 | Hanson et al. | |
| 2001/0041934 A1 * | 11/2001 | Yamazaki | A61M 60/196 |
| | | | 623/3.13 |
| 2003/0233021 A1 | 12/2003 | Nose et al. | |
| 2006/0024182 A1 * | 2/2006 | Akdis | A61M 60/237 |
| | | | 417/357 |
| 2006/0222533 A1 | 10/2006 | Reeves et al. | |
| 2008/0114339 A1 | 5/2008 | McBride et al. | |
| 2009/0060743 A1 | 3/2009 | McBride et al. | |
| 2009/0093764 A1 | 4/2009 | Pfeffer et al. | |
| 2009/0171137 A1 | 7/2009 | Farnan et al. | |
| 2011/0237863 A1 | 9/2011 | Ricci et al. | |
| 2011/0238172 A1 * | 9/2011 | Akdis | A61M 60/237 |
| | | | 623/3.11 |
| 2012/0089225 A1 * | 4/2012 | Akkerman | A61M 60/422 |
| | | | 623/3.13 |
| 2013/0338559 A1 | 12/2013 | Franano et al. | |

(56)                References Cited

U.S. PATENT DOCUMENTS

| | | | |
|---|---|---|---|
| 2014/0010686 A1 | 1/2014 | Tanner et al. | |
| 2014/0336446 A1* | 11/2014 | Rodefeld | A61M 60/148 |
| | | | 600/16 |
| 2016/0193396 A1* | 7/2016 | Taskin | A61M 60/806 |
| | | | 600/16 |
| 2016/0271308 A1 | 9/2016 | Larose et al. | |
| 2017/0043074 A1 | 2/2017 | Siess | |
| 2017/0296725 A1 | 10/2017 | Peters et al. | |
| 2018/0169312 A1* | 6/2018 | Barry | A61M 60/824 |
| 2018/0303990 A1 | 10/2018 | Siess et al. | |
| 2018/0311423 A1 | 11/2018 | Zeng et al. | |
| 2019/0275224 A1 | 9/2019 | Hanson et al. | |
| 2020/0306434 A1 | 10/2020 | VanCamp et al. | |
| 2020/0376182 A1* | 12/2020 | Siess | A61M 60/13 |
| 2021/0015982 A1 | 1/2021 | Kerkhoffs et al. | |
| 2021/0023282 A1 | 1/2021 | Siess et al. | |
| 2021/0038785 A1 | 2/2021 | Siess et al. | |
| 2021/0069393 A1 | 3/2021 | Schauer et al. | |
| 2021/0106810 A1 | 4/2021 | Pfeffer et al. | |
| 2022/0008714 A1* | 1/2022 | Stotz | A61M 60/806 |
| 2022/0080180 A1* | 3/2022 | Siess | A61M 60/806 |
| 2022/0134082 A1 | 5/2022 | Pfeffer et al. | |
| 2022/0384070 A1 | 12/2022 | Mourran | |
| 2023/0040593 A1 | 2/2023 | Liu et al. | |

FOREIGN PATENT DOCUMENTS

| | | | |
|---|---|---|---|
| EP | 2301598 B1 | 7/2017 | |
| EP | 3352808 B1 | 9/2023 | |
| JP | H06346917 A * | 12/1994 | A61M 60/829 |
| WO | 9500185 A1 | 1/1995 | |
| WO | 0117581 A2 | 3/2001 | |

OTHER PUBLICATIONS

Clarivate Analytics, machine translation of JP H96346917_A (Year: 2025).*

International Search Report and Written Opinion for International Application No. PCT/US2022/050053, dated Mar. 6, 2023. (110 pages).

* cited by examiner

PERCUTANEOUS CIRCULATORY SUPPORT DEVICE FACILITATING REDUCED HEMOLYSIS

CROSS REFERENCE TO RELATED APPLICATION

This application claims priority to Provisional Application No. 63/272,459, filed Oct. 27, 2021, which is herein incorporated by reference in its entirety.

TECHNICAL FIELD

The present disclosure relates to percutaneous circulatory support systems. More specifically, the disclosure relates to percutaneous circulatory support devices that facilitate reduced hemolysis and/or related complications.

BACKGROUND

Percutaneous circulatory support devices can provide transient support for up to approximately several weeks in patients with compromised heart function or cardiac output. Operation of such devices, however, may cause some amount of hemolysis (that is, the rupture or destroying of blood cells) or other complications. Hemolysis can in turn cause thrombi formation or other complications. Accordingly, there is a need for improved devices that facilitate reduced hemolysis and/or related corn plications.

SUMMARY

In an Example 1, a percutaneous circulatory support device comprises an impeller disposed within an impeller housing, the impeller being rotatable relative to the impeller housing to cause blood to flow through the percutaneous circulatory support device; and a liquid carrier carrying a liquid, and the liquid carrier being rotatable relative to the impeller housing to cause the liquid to form outwardly extending menisci at a plurality of apertures of the liquid carrier.

In an Example 2, the percutaneous circulatory support device of Example 1, further comprising a motor operatively coupled to the impeller and rotating the impeller relative to the impeller housing to cause blood to flow through the percutaneous circulatory support device.

In an Example 3, the percutaneous circulatory support device of Example 2, wherein the motor is further operatively coupled to the liquid carrier, the motor rotating the liquid carrier and the impeller together relative to the impeller housing.

In an Example 4, the percutaneous circulatory support device of Example 3, further comprising a driving magnet operatively coupled to the motor, the liquid carrier comprising a magnetic material and acting as a driven magnet, the driven magnet being operatively coupled to the driving magnet, and the motor rotates the liquid carrier and the impeller together, via the driving magnet, relative to the impeller housing.

In an Example 5, the percutaneous circulatory support device of any of Examples 1-4, wherein the impeller housing comprises a plurality of outlet apertures each extending to a proximal end of the liquid carrier.

In an Example 6, the percutaneous circulatory support device of any of Examples 1-5, wherein the liquid comprises an emulsion.

In an Example 7, the percutaneous circulatory support device of Example 6, wherein the emulsion comprises a lipidic emulsion.

In an Example 8, the percutaneous circulatory support device of Example 6, wherein the emulsion comprises a triglyceride.

In an Example 9, the percutaneous circulatory support device of Example 6, wherein a proximal portion of the impeller comprises a flattened shape.

In an Example 10, a percutaneous circulatory support device comprises a housing; a motor coupled to the housing; a liquid carrier disposed within the housing, the liquid carrier being operatively coupled to the drive motor, the liquid carrier comprising an interior chamber and a plurality of apertures joining the interior chamber to an exterior of the liquid carrier, the interior chamber carrying a liquid; and an impeller disposed within the housing; wherein the motor is configured to rotatably drive the liquid carrier and the impeller together relative to the housing, the liquid carrier thereby causing the liquid to form outwardly extending menisci at the plurality of apertures, and the impeller thereby causing blood to flow through the percutaneous circulatory support device.

In an Example 11, the percutaneous circulatory support device of Example 10, wherein the liquid carrier comprises a cylindrical shape.

In an Example 12, the percutaneous circulatory support device of Example 11, wherein the plurality of apertures are disposed on a circumferential side of the cylindrical shape.

In an Example 13, the percutaneous circulatory support device of Example 12, wherein the plurality of apertures extend parallel to a longitudinal direction of the cylindrical shape.

In an Example 14, the percutaneous circulatory support device of any of Examples 10-13, further comprising a shaft disposed within the housing, the liquid carrier and the impeller being fixedly carried by the shaft.

In an Example 15, the percutaneous circulatory support device of any of Examples 10-14, wherein a proximal portion of the impeller comprises a flattened shape.

In an Example 16, a percutaneous circulatory support device comprises an impeller housing; an impeller disposed within the impeller housing, the impeller being rotatable relative to the impeller housing to cause blood to flow through the percutaneous circulatory support device; and a liquid carrier disposed within the impeller housing, the liquid carrier comprising an interior chamber and a plurality of apertures joining the interior chamber to an exterior of the liquid carrier, the interior chamber carrying a liquid, and the liquid carrier being rotatable relative to the impeller housing to cause the liquid to form outwardly extending menisci at the plurality of apertures.

In an Example 17, the percutaneous circulatory support device of Example 16, further comprising a motor operatively coupled to the impeller and rotating the impeller relative to the impeller housing to cause blood to flow through the percutaneous circulatory support device.

In an Example 18, the percutaneous circulatory support device of Example 17, wherein the motor is further operatively coupled to the liquid carrier, the motor rotating the liquid carrier and the impeller together relative to the impeller housing.

In an Example 19, the percutaneous circulatory support device of Example 18, further comprising a driving magnet operatively coupled to the motor, the liquid carrier comprising a magnetic material and acting as a driven magnet, the driven magnet being operatively coupled to the driving magnet, and the motor rotates the liquid carrier and the impeller together, via the driving magnet, relative to the impeller housing.

In an Example 20, the percutaneous circulatory support device of Example 19, wherein the impeller housing comprises a plurality of outlet apertures each extending to a proximal end of the liquid carrier.

In an Example 21, the percutaneous circulatory support device of Example 16, wherein the liquid comprises an emulsion.

In an Example 22, the percutaneous circulatory support device of Example 21, wherein the emulsion comprises a lipidic emulsion.

In an Example 23, the percutaneous circulatory support device of Example 22, wherein the emulsion comprises a triglyceride.

In an Example 24, the percutaneous circulatory support device of Example 16, wherein a proximal portion of the impeller comprises a flattened shape.

In an Example 25, a percutaneous circulatory support device comprises a housing; a motor coupled to the housing; a driving magnet operatively coupled to the motor; a liquid carrier disposed within the housing, the liquid carrier comprising a magnetic material and being operatively coupled to the drive motor, the liquid carrier comprising an interior chamber and a plurality of apertures joining the interior chamber to an exterior of the liquid carrier, the interior chamber carrying a liquid; and an impeller disposed within the housing; wherein the motor is configured to rotatably drive, via the driving magnet, the liquid carrier and the impeller together relative to the housing, the liquid carrier thereby causing the liquid to form outwardly extending menisci at the plurality of apertures, and the impeller thereby causing blood to flow through the percutaneous circulatory support device.

In an Example 26, the percutaneous circulatory support device of Example 24, wherein the liquid carrier comprises a cylindrical shape.

In an Example 27, the percutaneous circulatory support device of Example 25, wherein the plurality of apertures are disposed on a circumferential side of the cylindrical shape.

In an Example 28, the percutaneous circulatory support device of Example 26, wherein the plurality of apertures extend parallel to a longitudinal direction of the cylindrical shape.

In an Example 29, the percutaneous circulatory support device of Example 24, further comprising a shaft disposed within the housing, the liquid carrier and the impeller being fixedly carried by the shaft.

In an Example 30, the percutaneous circulatory support device of Example 24, wherein a proximal portion of the impeller comprises a flattened shape.

In an Example 31, a method for using a percutaneous circulatory support device comprises positioning the percutaneous circulatory support device at a target location within a patient; rotating an impeller of the percutaneous circulatory support device to cause blood to flow through the percutaneous circulatory support device; and rotating a liquid carrier of the percutaneous circulatory support device to cause a liquid carried by the liquid carrier to form outwardly extending menisci at a plurality of apertures of the liquid carrier, the liquid thereby creating positive pressure that at least partially counteracts pressure created by the impeller.

In an Example 32, the method of Example 31, wherein the percutaneous circulatory support device further comprises a housing, and rotating the impeller and rotating the liquid carrier comprise rotating the impeller and the liquid carrier together relative to the housing.

In an Example 33, the method of Example 32, wherein the percutaneous circulatory support device further comprises a motor operatively coupled to the liquid carrier and the impeller, and rotating the impeller and the liquid carrier together relative to the housing comprises driving the impeller and the liquid carrier via the motor.

In an Example 34, the method of Example 33, wherein the percutaneous circulatory support device further comprises a driving magnet operatively coupled to the motor, the liquid carrier comprises a magnetic material and operatively couples to the driving magnet, and rotating the impeller and the liquid carrier together relative to the housing comprises driving the impeller and the liquid carrier via the motor and the driving magnet.

In an Example 35, the method of Example 31, wherein the liquid comprises an emulsion.

While multiple embodiments are disclosed, still other embodiments of the present invention will become apparent to those skilled in the art from the following detailed description, which shows and describes illustrative embodiments of the invention. Accordingly, the drawings and detailed description are to be regarded as illustrative in nature and not restrictive.

Figure 1:
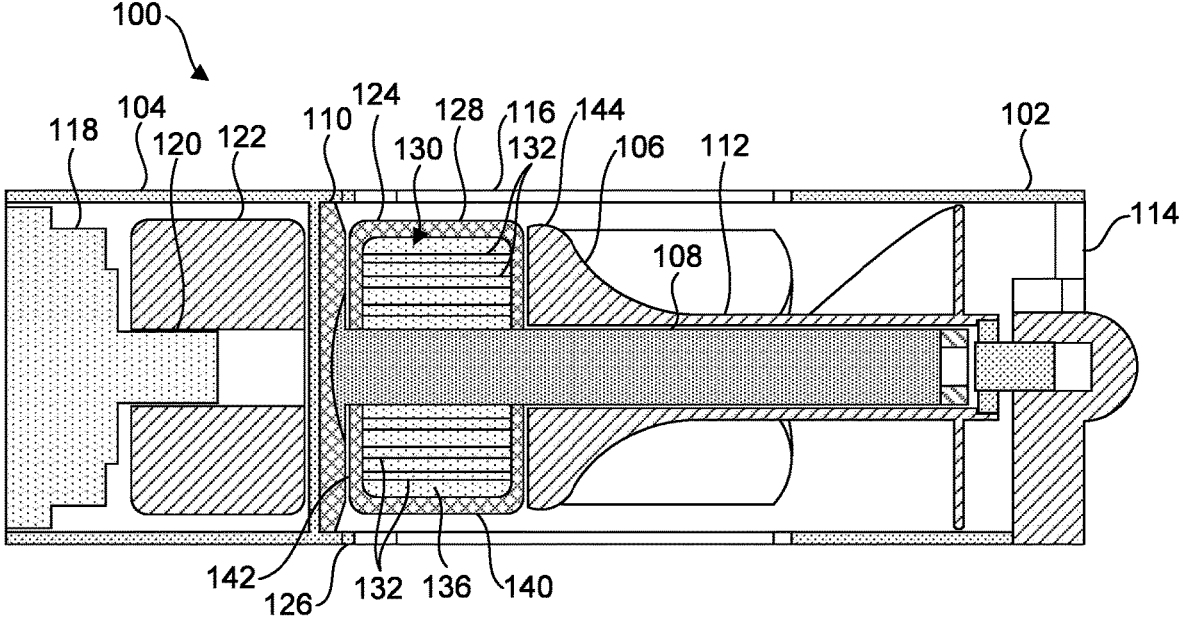
FIG. 1 is a side sectional view of an illustrative mechanical circulatory support device (also referred to herein, interchangeably, as a "blood pump"), in accordance with embodiments of the subject matter disclosed herein.

While the invention is amenable to various modifications and alternative forms, specific embodiments have been shown by way of example in the drawings and are described in detail below. The intention, however, is not to limit the invention to the particular embodiments described. On the contrary, the invention is intended to cover all modifications, equivalents, and alternatives falling within the scope of the invention as defined by the appended claims.

DETAILED DESCRIPTION

FIG. 1 depicts a partial side sectional view of an illustrative mechanical circulatory support device 100 (also referred to herein, interchangeably, as a "blood pump") in accordance with embodiments of the subject matter disclosed herein. The device 100 may form part of a percutaneous circulatory support system, together with a guidewire and an introducer sheath (not shown). More specifically, the guidewire and the introducer sheath may facilitate percutaneously delivering the device 100 to a target location within a patient, such as within the patient's heart. Alternatively, the device 100 may be delivered to a different target location within a patient.

Figure 2:
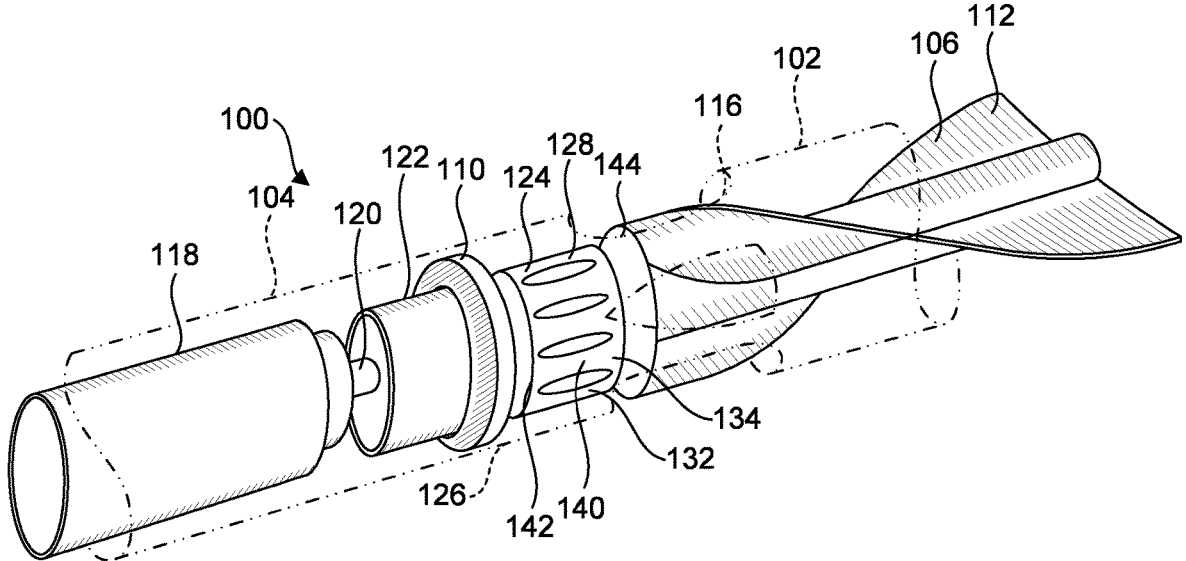
FIG. 2 is a perspective view of the mechanical circulatory support device of FIG. 1, with housing components of the device shown in phantom lines, in accordance with embodiments of the subject matter disclosed herein.

With continued reference to FIG. 1 and additional reference to FIG. 2, the device 100 generally includes an impeller housing 102 and a motor housing 104. In some embodiments, the impeller housing 102 and the motor housing 104 may be integrally or monolithically constructed. In other embodiments, the impeller housing 102 and the motor housing 104 may be separate components configured to be removably or permanently coupled.

The impeller housing 102 carries an impeller assembly 106 therein. The impeller assembly 106 includes an impeller shaft 108 (FIG. 1) that is rotatably supported by at least one bearing, such as a bearing 110. The impeller assembly 106 also includes an impeller 112 that rotates relative to the impeller housing 102 to drive blood through the device 100. More specifically, the impeller 112 causes blood to flow from a blood inlet 114 (FIG. 1) formed on the impeller housing 102, through the impeller housing 102, and out of a blood outlet 116 formed on the impeller housing 102. In some embodiments and as illustrated, the impeller shaft 108 and the impeller 112 may be separate components, and in other embodiments the impeller shaft 108 and the impeller 112 may be integrated. In some embodiment and as illustrated, the inlet 114 and/or the outlet 116 may each include multiple apertures. In other embodiments, the inlet 114 and/or the outlet 116 may each include a single aperture. In some embodiments and as illustrated, the inlet 114 may be formed on an end portion of the impeller housing 102 and the outlet 116 may be formed on a side portion of the impeller housing 102. In other embodiments, the inlet 114 and/or the outlet 116 may be formed on other portions of the impeller housing 102. In some embodiments, the impeller housing 102 may couple to a distally extending cannula (not shown), and the cannula may receive and deliver blood to the inlet 114.

With continued reference to FIGS. 1 and 2, the motor housing 104 carries a motor 118, and the motor 118 is configured to rotatably drive the impeller 112 relative to the impeller housing 102. In the illustrated embodiment, the motor 118 rotates a drive shaft 120, which is coupled to a driving magnet 122. Rotation of the driving magnet 122 causes rotation of a liquid carrier 124, which is constructed of a magnetic material and acts as a driven magnet. The liquid carrier 124 is connected to and rotates together with the impeller assembly 106. More specifically, in embodiments incorporating the impeller shaft 108, the impeller shaft 108 and the impeller 112 are configured to rotate with the liquid carrier 124. In other embodiments, the motor 118 may couple to the impeller assembly 106 via other components. For example, the motor 118 may couple to the impeller assembly 106 via the driving magnet 122 and a driven magnet (not shown) formed separately from the liquid carrier 124.

In some embodiments, a controller (not shown) may be operably coupled to the motor 118 and configured to control the motor 118. In some embodiments, the controller may be disposed within the motor housing 104. In other embodiments, the controller may be disposed outside of the motor housing 104 (for example, in a catheter handle, an independent housing, etc.). In some embodiments, the controller may include multiple components, one or more of which may be disposed within the motor housing 104. According to embodiments, the controller may be, may include, or may be included in one or more Field Programmable Gate Arrays (FPGAs), one or more Programmable Logic Devices (PLDs), one or more Complex PLDs (CPLDs), one or more custom Application Specific Integrated Circuits (ASICs), one or more dedicated processors (e.g., microprocessors), one or more Central Processing Units (CPUs), software, hardware, firmware, or any combination of these and/or other components. Although the controller is referred to herein in the singular, the controller may be implemented in multiple instances, distributed across multiple computing devices, instantiated within multiple virtual machines, and/or the like. In other embodiments, the motor 118 may be controlled in other manners.

Figures 3, 4:
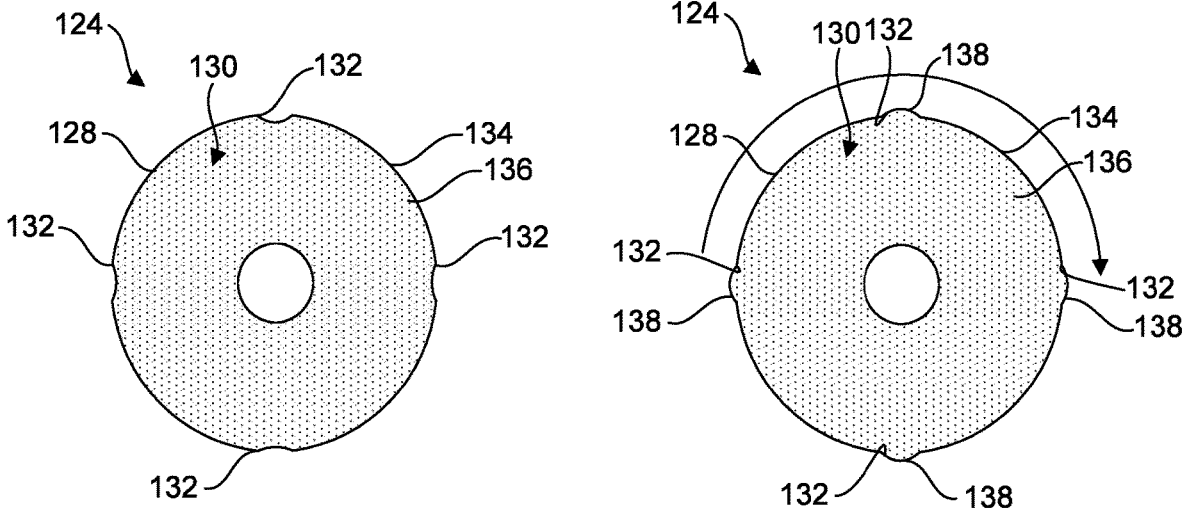
FIG. 3 is a cross-sectional view of a liquid carrier of the mechanical circulatory support device of FIG. 1 while the liquid carrier is stationary relative to housing components of the device, in accordance with embodiments of the subject matter disclosed herein.
FIG. 4 is a cross-sectional view of the liquid carrier of the mechanical circulatory support device of FIG. 1 while the liquid carrier rotates relative to housing components of the device, in accordance with embodiments of the subject matter disclosed herein.

With further reference to FIGS. 1 and 2 and additional reference to FIGS. 3 and 4, the device 100 facilitates reduced device-induced hemolysis compared to conventional devices. More specifically, rotation of the liquid carrier 124 inhibits blood from entering small voids of a proximal end portion 126 of the impeller housing 102, which reduces hemolysis. As shown in FIGS. 3 and 4, the liquid carrier 124 includes a wall 128 that surrounds an interior chamber 130. One or more apertures 132 (only four apertures 132 being illustrated in FIGS. 3 and 4) are formed in the wall 128 and join the interior chamber 130 to the exterior 134 of the liquid carrier 124. The interior chamber 130 carries a liquid 136. As shown in FIG. 3, when the liquid carrier 124 is stationary relative to the impeller housing 102, the liquid 136 remains within the interior chamber 130. However, and as shown in FIG. 4, when the liquid carrier 124 rotates (caused by rotation of the driving magnet 122 and together with the impeller assembly 106), centrifugal force causes the liquid 136 to form convex or outwardly extending menisci 138 at the plurality of apertures 132. The liquid 136 thereby creates positive pressure that at least partially counteracts pressure created by rotation of the impeller 112. The menisci 138 also contact the walls of the impeller housing 102 to function effectively as a seal at the proximal end portion 126 of the impeller housing 102 and, as described above, thereby partially or completely inhibit blood from entering the small voids of the proximal end portion 126. The menisci 138 may also reduce friction between the rotating components and the impeller housing 102.

With reference again to FIGS. 1 and 2, in some embodiments and as illustrated the liquid carrier 124 has cylindrical shape. In some embodiments and as illustrated, the plurality of apertures 132 are formed on a circumferential side 140 of the cylindrical shape. In some embodiments and as illustrated, the apertures 132 extend parallel to the longitudinal direction of the cylindrical shape. In other embodiments, the liquid carrier 124 may have different shapes, and/or the apertures 132 may have different shapes or arrangements.

The liquid 136 may comprise any of various liquids that are capable of forming menisci when subjected to centrifugal force and appropriate for intravenous use. For example, the liquid 136 may be an emulsion, more specifically a lipidic emulsion, such as a triglyceride. In other embodiments, the liquid 136 may take other forms. For example, the liquid 136 may be a viscous solution including concentrated sugars, such as fruit syrup or fruit extract. Such fruit extract may be, for example, date palm fruit extract comprising unsaturated fatty acids, such as oleic acid (44.51 g/100 g), palmitic acid (23.05 g/100 g), and linoleic acid (11.66 g/100 g). In some embodiments, including the fruit-based solutions described above, the liquid 136 may also act as a lubricant for the moving components of the device 100.

The device 100 may also include one or more additional features that facilitate reduced device-induced hemolysis compared to conventional devices. For example, and referring to FIGS. 1 and 2, the apertures of the outlet 116 may be relatively long compared to those of conventional devices. More specifically, the apertures of the outlet 116 may each extend to a proximal end 142 of the liquid carrier 124. Such apertures inhibit blood from pooling in the proximal end portion 126 of the impeller housing 102, which reduces hemolysis and/or thrombosis. As another example and still referring to FIGS. 1 and 2, a proximal portion 144 of the impeller 112 may have a flattened shape, in contrast to lips or peaks of the impellers of conventional devices. Such a shape inhibits blood from forming and pooling in vortices adjacent to the impeller 112.

Various modifications and additions can be made to the exemplary embodiments discussed without departing from the scope of the present invention. For example, while the embodiments described above refer to particular features, the scope of this invention also includes embodiments having different combinations of features and embodiments that do not include all of the described features. Accordingly, the scope of the present invention is intended to embrace all such alternatives, modifications, and variations as fall within the scope of the claims, together with all equivalents thereof.

We claim:

1. A percutaneous circulatory support device, comprising:
an impeller housing;
an impeller disposed within the impeller housing, the impeller being rotatable relative to the impeller housing to cause blood to flow through the percutaneous circulatory support device;
a viscous liquid that is not blood; and
a liquid carrier disposed within the impeller housing, the liquid carrier comprising an interior chamber having the liquid located therein and a plurality of apertures joining the interior chamber to an exterior of the liquid carrier, the liquid carrier being rotatable relative to the impeller housing to cause the liquid to form outwardly extending menisci at the plurality of apertures and seal a proximal portion of the impeller housing from blood during rotation of the liquid carrier,
wherein the plurality of apertures are disposed proximal of the impeller.

2. The percutaneous circulatory support device of claim 1, further comprising a motor operatively coupled to the impeller and rotating the impeller relative to the impeller housing to cause blood to flow through the percutaneous circulatory support device.

3. The percutaneous circulatory support device of claim 2, wherein the motor is further operatively coupled to the liquid carrier, the motor rotating the liquid carrier and the impeller together relative to the impeller housing.

4. The percutaneous circulatory support device of claim 3, further comprising a driving magnet operatively coupled to the motor, the liquid carrier comprising a magnetic material and acting as a driven magnet, the driven magnet being operatively coupled to the driving magnet, and the motor rotates the liquid carrier and the impeller together, via the driving magnet, relative to the impeller housing.

5. The percutaneous circulatory support device of claim 4, wherein the impeller housing comprises a plurality of outlet apertures each extending to a proximal end of the liquid carrier.

6. The percutaneous circulatory support device of claim 1, wherein the liquid comprises an emulsion.

7. The percutaneous circulatory support device of claim 6, wherein the emulsion comprises a lipidic emulsion.

8. The percutaneous circulatory support device of claim 7, wherein the emulsion comprises a triglyceride.

9. The percutaneous circulatory support device of claim 1, wherein a proximal portion of the impeller comprises a flattened shape.

10. A percutaneous circulatory support device, comprising:
a housing;
a motor coupled to the housing;
a driving magnet operatively coupled to the motor;
a viscous liquid that is not blood; and
a liquid carrier disposed within the housing, the liquid carrier comprising a magnetic material and being operatively coupled to the drive motor, the liquid carrier comprising an interior chamber having the liquid located therein and a plurality of apertures joining the interior chamber to an exterior of the liquid carrier; and
an impeller disposed within the housing, the impeller comprising a plurality of blades extending radially therefrom;
wherein the motor is configured to rotatably drive, via the driving magnet, the liquid carrier and the impeller together relative to the housing, the liquid carrier thereby causing the liquid to form outwardly extending menisci at the plurality of apertures that contact a wall of the impeller housing to seal a proximal portion of the impeller housing from blood during rotation of the liquid carrier, and the impeller thereby causing blood to flow through the percutaneous circulatory support device;
wherein the plurality of apertures are disposed proximal of the plurality of blades.

11. The percutaneous circulatory support device of claim 10, wherein the liquid carrier comprises a cylindrical shape.

12. The percutaneous circulatory support device of claim 11, wherein the plurality of apertures are disposed on a circumferential side of the cylindrical shape.

13. The percutaneous circulatory support device of claim 12, wherein the plurality of apertures extend parallel to a longitudinal direction of the cylindrical shape.

14. The percutaneous circulatory support device of claim 10, further comprising a shaft disposed within the housing, the liquid carrier and the impeller being fixedly carried by the shaft.

15. The percutaneous circulatory support device of claim 10, wherein a proximal portion of the impeller comprises a flattened shape.

16. A method for using a percutaneous circulatory support device, comprising:
positioning the percutaneous circulatory support device at a target location within a patient, the percutaneous circulatory support device comprising a liquid carrier;
rotating an impeller of the percutaneous circulatory support device to cause blood to flow through the percutaneous circulatory support device; and
rotating the liquid carrier of the percutaneous circulatory support device having a viscous liquid located therewithin that is not blood to cause the liquid carried by the liquid carrier to form outwardly extending menisci at a plurality of apertures of the liquid carrier, the plurality of apertures disposed proximal of the impeller, the liquid thereby creating positive pressure that at least partially counteracts pressure created by the impeller and sealing a proximal portion of a housing of the impeller from blood during rotation of the liquid carrier.

17. The method of claim 16, wherein the percutaneous circulatory support device further comprises a housing, and rotating the impeller and rotating the liquid carrier comprise rotating the impeller and the liquid carrier together relative to the housing.

18. The method of claim 17, wherein the percutaneous circulatory support device further comprises a motor operatively coupled to the liquid carrier and the impeller, and rotating the impeller and the liquid carrier together relative to the housing comprises driving the impeller and the liquid carrier via the motor.

19. The method of claim 18, wherein the percutaneous circulatory support device further comprises a driving magnet operatively coupled to the motor, the liquid carrier comprises a magnetic material and operatively couples to the driving magnet, and rotating the impeller and the liquid carrier together relative to the housing comprises driving the impeller and the liquid carrier via the motor and the driving magnet.

20. The method of claim 16, wherein the liquid comprises an emulsion.

\* \* \* \* \*